United States Patent [19]
Caracciolo, Jr.

[11] Patent Number: 5,965,087
[45] Date of Patent: *Oct. 12, 1999

[54] SYSTEM AND METHOD FOR CONTROLLING MICROORGANISMS ASSOCIATED WITH POULTRY

[75] Inventor: Louis D. Caracciolo, Jr., Atco, N.J.

[73] Assignee: The BOC Group, Inc., Murray Hill, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/607,662

[22] Filed: Feb. 27, 1996

[51] Int. Cl.[6] .............................. A61L 2/20; A01K 45/00
[52] U.S. Cl. ............................ 422/28; 422/292; 119/6.8; 119/300; 119/677
[58] Field of Search ........................... 422/28, 123, 292; 119/6.8, 300, 651, 677; 426/320

[56] References Cited

U.S. PATENT DOCUMENTS

| | | | |
|---|---|---|---|
| 1,107,745 | 8/1914 | Batter | 422/4 X |
| 1,423,704 | 7/1922 | Wolff | 422/4 |
| 1,714,562 | 5/1929 | Keiser | 422/4 X |
| 1,932,379 | 10/1933 | Ballentine | 422/4 |
| 2,132,539 | 10/1938 | McRae | 422/4 X |
| 2,173,073 | 9/1939 | Pierson | 261/30 |
| 2,203,188 | 6/1940 | Beer | 422/4 |
| 2,245,762 | 6/1941 | De Stefani et al. | 422/24 X |
| 2,523,373 | 9/1950 | Jennings et al. | 422/124 |
| 3,107,974 | 10/1963 | Potapenko | 422/4 |
| 3,421,836 | 1/1969 | Sundin et al. | 422/4 |
| 3,505,989 | 4/1970 | Truhan | 422/4 X |
| 3,518,046 | 6/1970 | Cicirello | 422/4 |
| 3,681,008 | 8/1972 | Black | 422/117 |
| 3,721,067 | 3/1973 | Agnew | 422/4 X |
| 3,820,536 | 6/1974 | Anspach, Jr. et al. | 128/202.13 |
| 4,102,656 | 7/1978 | Koritz | 55/210 |
| 4,240,798 | 12/1980 | Wendelin et al. | 423/219 |
| 4,250,143 | 2/1981 | Bryan et al. | 422/109 |
| 4,435,194 | 3/1984 | Picard et al. | 95/19 |
| 4,932,359 | 6/1990 | Sheldon et al. | . |
| 5,234,703 | 8/1993 | Guthery | 426/331 |
| 5,311,841 | 5/1994 | Thaxton | . |
| 5,451,400 | 9/1995 | Stern et al. | 424/93.3 |
| 5,460,705 | 10/1995 | Murphy et al. | 204/252 |
| 5,493,994 | 2/1996 | Cox et al. | 426/47 X |

FOREIGN PATENT DOCUMENTS

2331359A1  2/1975  Germany .

OTHER PUBLICATIONS

"Continental Grain Licenses Natural Salmonella Blocker," Research News, Agricultural Services, USDA, Broiler Industry, Jul. 1995.

P.E. Whistler et al., "Bacterial Activity, Eggshell Conductance, and Hatchability of Ozone Versus Formaldehyde Disinfection," Dept. of Food Science, North Carolina State University, pp. 1074–1077 (Sep. 15, 1988).

Nurmi et al., Nature, vol. 241, pp. 210–211 (1973).

*Primary Examiner*—Elizabeth McKane
*Attorney, Agent, or Firm*—Finnegan, Henderson, Farabow, Garrett & Dunner, L.L.P.

[57] ABSTRACT

The present invention is directed to a system and method for controlling microorganisms on a surface in a hatchery. The present invention is also directed to a system and method for controlling microorganisms on the surface of eggs. The present invention is further directed to a method for reducing the level of pathogen infection in a poultry flock.

11 Claims, 1 Drawing Sheet

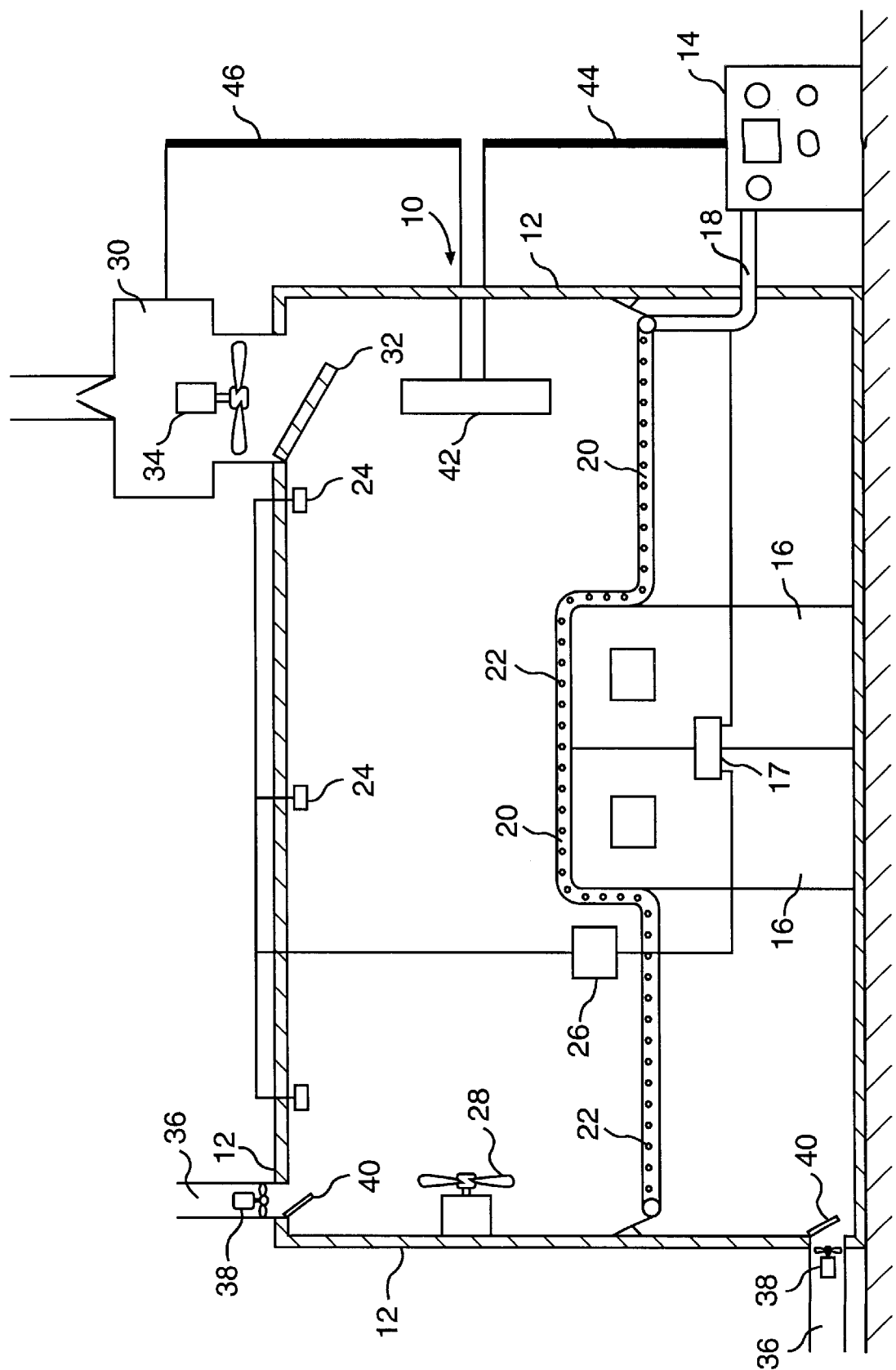

SYSTEM AND METHOD FOR CONTROLLING MICROORGANISMS ASSOCIATED WITH POULTRY

FIELD OF INVENTION

The present invention broadly relates to a system and method for controlling microorganisms associated with poultry. The present invention particularly relates to a method and system for controlling microorganisms on a surface in a hatchery. The present invention further particularly relates to a method and system for controlling microorganisms on the surface of eggs. The present invention further particularly relates to a method of reducing the level of pathogen infection in a poultry flock.

BACKGROUND OF THE INVENTION

Commercial flocks of poultry, such as chickens, turkeys, ducks, geese, quail and the like, can generally be classified as belonging to one of three flocks: the primary (or master) breeding flock, the secondary breeding flock, and the food flock. Poultry eggs can likewise be loosely classified into two general categories, hatching eggs, which are fertile eggs that are to be hatched into chicks (for the breeding flock or the food flock), and table eggs, which can be either fertile or infertile eggs that are intended for direct consumption.

The food flock, as its name implies, is intended for direct consumption, i.e., these are the birds that are purchased for food at a local grocery store. The secondary breeding flock produces both hatching eggs, from which the food flock is hatched, and table eggs intended for direct consumption. Birds are selected for membership in this flock based upon a number of factors, including the number and size of eggs produced and the characteristics of the birds hatched from these eggs (the food flock). The primary or master breeding flock also produces hatching eggs, from which the secondary breeding flock is hatched, but not table eggs. These birds are selected for membership in the master flock based upon their particular genetic characteristics as evidenced in the secondary breeding flock (second generation) and the food flock (third generation).

When food borne pathogens began to pose a major health issue, the poultry industry began to experience public pressure to remedy the problem of these pathogens. It has been found that a primary source of pathogen infection in chicks is the hatchery. Indeed, it is well documented that after a chick has been hatched, the chances are over 90% that it is a carrier of a number of pathogens which are dangerous to both consumers and other poultry in the flock (breeding or food). These pathogens include Salmonella spp. and Campylobacter spp., both of which have caused numerous cases of human intestinal diseases.

Even with the high probability of pathogen infection at hatching, the natural resistance to infection that develops in growing poultry nevertheless reduces the percentage of infected birds in the overall flock population. For example, in the case of salmonella, the percentage of contaminated chicks in the flock will drop from 90% of the population immediately following hatching to about 26% of the population in the houses in which the birds are grown and/or maintained. The effect of this bird's natural resistance is even more pronounced when the incidence of pathogen infection at hatching is reduced. For example, research has shown that chicks which are not infected with salmonella at hatching will resist infection during the period they are growing (e.g., 60 days or so) even if the grow house is contaminated.

The residual contaminated birds, however, remain a source of pathogen infection for the rest of the flock, breeding or food.

Moreover, in the case of the food flock, these residual contaminated birds are the most likely source of dangerous food borne pathogens when the flock is harvested.

A process known as competitive exclusion was proposed by Nurmi and Rantala, *Nature*, vol. 241, pp. 210–211 (1973), as a means for reducing the level of pathogen infection in poultry. This process involves administering intestinal bacteria from mature, healthy poultry to chicks whose intestinal bacteria were not yet established. The bacteria administered to the chicks competes with any pathogens that might be present in the gut of the chick, reducing the rate of colonization by the pathogens and thus the level of infection.

This method, however, has not provided completely satisfactory results. For example, the competing bacteria administered to the chicks may not colonize at a sufficient level to satisfactorily reduce the rate of colonization by the pathogen. In addition, over time, the pathogens tend to adapt to the presence of the competing bacteria and can actually colonize at a faster rate, thereby out-competing the competitive bacteria.

Thus, while the poultry industry has responded by treating many of the symptoms of the problems of pathogens, no practical solution has been offered which will cure the problem at its source: the hatchery. Accordingly, there remains a need for a system and method for controlling microorganisms associated with poultry.

SUMMARY OF THE INVENTION

The present invention is directed to a method and system for controlling microorganisms on a surface in a hatchery. The present invention is also directed to a method and system for controlling microorganisms on the surface of eggs. The present invention is further directed to a method for reducing the level of pathogen infection in a poultry flock.

Additional features and advantages of the invention will be set forth in the description which follows, and in part will be apparent from the description or may be learned from practice of the invention. The advantages of the invention will be realized and attained by the method and apparatus particularly pointed out in the written description and claims.

To achieve these and other advantages and in accordance with the purpose of the invention, as embodied and broadly described, the invention provides a method of controlling microorganisms on a surface in a hatchery by contacting the surface with an effective amount of a source of ozone for a time sufficient to control the microorganisms. The present invention further provides a system for controlling microorganisms on a surface in a hatchery comprising means for regulating the atmosphere surrounding the surface and means for introducing a source of ozone into this atmosphere.

The present invention also provides a method for controlling microorganisms on the surface of an egg by contacting the surface of the egg with a sufficient amount of a source of ozone for a sufficient amount of time. In a preferred embodiment, this method will increase the hatchability of the eggs whose surfaces are contacted with the source of ozone. The present invention further provides a system for controlling microorganisms on the surface of an egg comprising means for regulating the atmosphere surrounding the surface of the egg and means for introducing a source of ozone into this atmosphere.

The present invention also provides a method for reducing the level of pathogen infection in a poultry flock by contacting eggs which are to be hatched with a source of ozone for a time sufficient to control microorganisms on the surfaces of the eggs.

It is to be understood that both the foregoing general description and the following detailed description are exemplary and explanatory and are intended to provide further explanation of the invention as claimed.

BRIEF DESCRIPTION OF THE DRAWING

For a fuller understanding of the invention, reference is made to the following detailed description taken in connection with the accompanying drawing in which:

The FIGURE is an elevation, partly in section, of a hatchery as a preferred system associated with the method of the present invention.

DETAILED DESCRIPTION OF PREFERRED EMBODIMENTS

A first embodiment of the present invention is directed to a method of controlling microorganisms on a surface in a hatchery by contacting the surface with a source of ozone. The surface in the hatchery may be any of the surfaces generally found in a hatchery on which it is desired to control one or microorganisms. For example, the surface in the hatchery may be a wall and/or floor of the hatchery. Alternatively, the surface in the hatchery may be the surface of an egg which is in, or intended to be placed in, the hatchery.

According to the present invention, "controlling" microorganisms includes both the reduction and/or prevention of the growth of one or more microorganisms. It is to be further understood that by "controlling" microorganisms, the growth and/or reproduction of the microorganisms is inhibited i.e., there is substantially no growth of the microorganisms. "Controlling" microorganisms also includes maintaining a microorganism population at a desired level (including undetectable levels such as zero population), reducing a microorganism population to a desired level and/or inhibiting or slowing the growth of a microorganism population. Increasing the hatchability of the eggs whose shell surfaces are contacted with the source of ozone is intended to mean that the percent hatch of treated fertile eggs will be greater than that of untreated fertile eggs.

Also according to the present invention, "source of ozone" is intended to mean any suitable form of ozone for use in the present method, including, but not limited to an ozonated gas, such as gaseous ozone or ozonated air, or a material that generates ozone in situ upon contact with the surface. Preferably, the source of ozone is gaseous ozone or ozonated air.

Preferably, for additional control of microorganisms, an effective amount of one or more other suitable gas may also be introduced, either alone or included in a mixture with the source of ozone. Illustrative examples of these other suitable gases include, but are not limited to, argon, nitrogen, carbon dioxide and carbon monoxide.

The source of ozone is employed in an amount that will provide an effective level of ozone to control microorganisms on a surface in a hatchery. One skilled in the art can determine through available methods an appropriate amount of the source of ozone and/or other suitable gas based upon the particular application of the inventive method and the particular source of ozone and/or other gas employed. Preferably, the amount of the source of ozone employed is sufficient to raise the concentration of ozone in the atmosphere immediately surrounding the surface in a hatchery to from about 2 to about 4 parts per million (ppm). More preferably, when the source of ozone is ozonated air, the concentration of ozone in the ozonated air is about 2 to 4 ppm.

The surface in a hatchery on which control of microorganisms is desired should be contacted with the source of ozone for a time sufficient to control the microorganisms on the surface. The particular time selected will depend upon a variety of factors, such as the source of ozone employed, the concentration of ozone on the surface, the number and type of microorganisms that are to be controlled, the particular surface being treated and the level of control desired. One skilled in the art can readily determine the appropriate contact time based upon the particular application of the inventive method. Preferably, the contact time is between 5 and 30 minutes, more preferably about 20 minutes.

In a preferred embodiment of the inventive method, the surface in a hatchery is the surface of an egg that has been placed in the hatchery for hatching. According to this preferred embodiment, the surface of one or more eggs is contacted with a source of ozone for a time sufficient to control microorganisms on the surface of the egg(s). More preferably, the contact is sufficient to increase the hatchability of the egg(s). Particularly preferably, gaseous ozone or ozonated air is introduced into the atmosphere of a hatchery containing one or more eggs for a time sufficient for the level of ozone in the atmosphere to reach an effective level, preferably from 2 to 4 ppm, to control the microorganisms on the surface of the egg(s).

More preferably, following contacting the egg(s) with the source of ozone for a time sufficient to control the microorganisms on their surface, a poultry gut serum is applied to the surface of the egg(s). The poultry gut serum is applied after the level of ozone in the atmosphere is reduced to an innocuous level.

The poultry gut serum employed in the present invention may be any formulation that contains an effective amount of one or more desired poultry microorganisms. For example, a natural poultry gut serum may be prepared by extracting microorganisms such as bacteria from the intestines of healthy poultry, i.e., poultry free of salmonella bacteria and other such pathogens. These extracts are then cultured for a sufficient time to provide the necessary level of microorganisms for implantation. Alternatively, a gut serum may be prepared employing genetically engineered microorganisms such as bacteria, or combinations of natural and genetically engineered microorganisms.

The poultry gut serum may also contain suitable amounts of other active agents and additives as desired. Illustrative examples of other such agents and additives include, but are not limited to, hormones (e.g., growth hormones), nutrients (e.g., yeast, carbohydrates, proteins and the like), and immunomodulating agents (e.g., vaccines and antibiotics).

The poultry gut serum is preferably applied to eggs by preparing an aqueous solution or suspension of the serum and then contacting, e.g., by spraying, one or more eggs with this solution or suspension. When a hatching chick pips out, it consumes some of this poultry gut serum. The poultry gut serum implants in the gut of the hatching chick competitive bacteria and the like to help reduce the likelihood of subsequent infection of poultry by pathogenic microorganisms.

An example of a suitable poultry gut serum is described in U.S. Pat. No. 5,451,400, which is herein incorporated by reference.

Another aspect of this embodiment of the present invention is directed to a system for controlling microorganisms on a surface in a hatchery. The inventive system comprises means for regulating the atmosphere surrounding the surface and means for introducing a source of ozone into the atmosphere. According to the present invention, "regulating the atmosphere surrounding the surface" is intended to mean minimizing any exchange between the atmosphere surrounding the surface and the external atmosphere. Illustrative examples of suitable means include, but are not limited to, enclosures, gas streams such as mixtures of ozone and one or more other suitable gases, and the like.

Preferably, when the surface in a hatchery is an egg, the means for controlling the atmosphere surrounding the egg is an enclosure dimensioned to contain one or more eggs and the means for introducing a source of ozone is an ozone generator.

A particularly preferred embodiment of the present inventive system is depicted in the accompanying drawing. Referring to the figure, means for controlling the atmosphere surrounding an egg is a hatchery 10 having a multiplicity of walls 12 constructed of any suitable material, such as wood, concrete or stainless steel. Preferably, walls 12 are constructed of a material which is impervious to ozone, such as stainless steel.

Hatchery 10 is constructed in such a manner as to control the atmosphere surrounding the egg or eggs, i.e., to minimize exchange between the atmosphere surrounding the egg or eggs and the external atmosphere. Preferably, hatchery 10 is constructed in such a manner that it is completely enclosed. More preferably, hatchery 10 is constructed to be substantially air tight, i.e., the flow of gases between the internal atmosphere of hatchery 10 and the external atmosphere is minimized. Hatchery 10 is provided with means 14 for supplying a source of ozone. Preferably, means 14 for supplying a source of ozone is an ozone generator providing ozonated gas.

At least one of walls 12 is preferably provided with an opening, such as a door or doors 16, to allow for persons and poultry to enter and exit hatchery 10. Preferably, doors 16 are provided in such a manner as to form a substantially air tight seal with the wall 12 to minimize the flow of gases between the internal atmosphere of hatchery 10 and the external atmosphere. Doors 16 are preferably provided with locking means 17 to prevent entry while the internal atmosphere of hatchery 10 contains high concentrations of ozone.

In a more particularly preferred embodiment of the inventive hatchery, means 14 for supplying a source of ozone is positioned remote to hatchery 10, i.e., outside of hatchery 10. In such a particularly preferred embodiment, there is further provided means 18 for introducing a source of ozone into the internal atmosphere of hatchery 10. Preferably, means 18 for introducing a source of ozone includes an ozone injection system, such as one or more pipes 20 distributed along one or more of walls 12. A source of ozone such as ozonated gas may be introduced into the internal atmosphere of hatchery 10, for example, through a multiplicity of holes 22 in pipe 20. Hatchery 10 may also include means (not shown) for introducing one or more other suitable gases, such as argon, oxygen and/or nitrogen, either alone or in admixture with other gases and/or the source of ozone.

Means 14 for supplying a source of ozone should be of sufficient efficiency to provide an effective amount of the source of ozone for a sufficient time to control a microorganism on a surface in the hatchery, such as the surface of an egg. Preferably, the means 14 for supplying a source of ozone is of sufficient capacity to provide a concentration of about 2 to 4 ppm of ozone in the internal atmosphere of hatchery 10 for a period of up to about 20 minutes.

Preferably, hatchery 10 is further provided with means 24 for determining the concentration of ozone in the internal atmosphere of hatchery 10. Preferably, means 24 for determining the concentration of ozone is one or more ozone sensors. In a particularly preferred embodiment of inventive hatchery 10, a multiplicity of ozone sensors is distributed throughout the internal atmosphere of the hatchery.

Means 24 for determining the concentration of ozone preferably includes means (not shown) for regulating the concentration of ozone. Preferably, the means for regulating the concentration of ozone adjusts the flow of the source of ozone from the means 14 for supplying a source of ozone and/or through means 18 for introducing a source of ozone to conform the concentration of ozone in the internal atmosphere of hatchery 10 to a predetermined level.

In a particularly preferred embodiment of inventive hatchery 10, means 24 for determining the concentration of ozone further includes means 26 for displaying the concentration of ozone. Preferably, means 26 for displaying the concentration of ozone is an ozone monitor, which displays the concentration of ozone in the internal atmosphere of hatchery 10 at each point where a means 24 for determining the concentration of ozone is located.

Hatchery 10 may further be provided with means 28 for assisting ozone distribution throughout the internal atmosphere of hatchery 10. Preferably, means 28 for assisting ozone distribution is one or more fans located at various points throughout hatchery 10. Means 28 for assisting ozone distribution may be selectively operated, for example, to generate currents in the internal atmosphere of hatchery 10 to more evenly distribute the source of ozone.

Hatchery 10 is also preferably provided with means 30 for reducing the concentration of ozone in the internal atmosphere of hatchery 10 to a safe level. Preferably, means 30 for reducing the concentration of ozone is a ventilation scrubber system, which removes and destroys ozone in hatchery 10.

Ventilation scrubber system of means 30 preferably comprises an air tight ventilation door 32 in wall 12 and an exhaust fan 34. Exhaust fan 34 is preferably disposed such that when it is activated, it draws gases from the internal atmosphere of hatchery 10 through ventilation door 32. The gases drawn from the internal atmosphere of hatchery 10 are preferably routed through means (not shown) for destroying ozone prior to release of the gases to the external atmosphere.

Preferably, means 30 for reducing the concentration of ozone further includes inlet means 36 for introducing air from the external atmosphere into the internal atmosphere of hatchery 10. More preferably, inlet means 36 may also be used to introduce oxygen-rich gas into the internal atmosphere during and/or after reduction of the concentration of ozone. Preferably, inlet means 36 may be adapted to open upon activation of means 30 as a ventilation scrubber system. Inlet means 36 are preferably sealed during the ozonization of the hatching. When opened, inlet means 36 allow fresh non-ozonated air from the external atmosphere and/or oxygen-rich gas into the internal atmosphere of hatchery 10 by the currents created by exhaust fan 34. More preferably, it is the oxygen-rich gas, such as oxygen-rich air, which is introduced at this time into the internal atmosphere of hatchery 10.

To facilitate the flow of fresh air and/or oxygen-rich gas into the hatchery, inlet means 36 are preferably provided with inlet fans 38 and inlet doors 40. More preferably, means 28 for assisting ozone distribution may also be activated to improve circulation of the air and/or oxygen-rich gas during reduction of the concentration of ozone in the internal atmosphere.

Hatchery 10 is further preferably provided with means 42 for detecting pip out of hatching chicks. Preferably, means 42 for detecting pip out is a sensitive motion detector such as a strain gauge generator. The means 42 for detecting pip out is preferably operatively linked via means 44 to means 14 for supplying a source of ozone such that, when pip out commences, the flow of ozone from means 14 and/or means 18 for introducing ozone is regulated such that the concentration of ozone in the internal atmosphere of hatchery 10 is not harmful to the hatching chicks. Means 42 for detecting pip out is also preferably operatively linked via means 46 to means 30 for reducing the concentration of ozone in the internal atmosphere of hatchery 10 such that, when pip out commences, the concentration of ozone in the internal atmosphere of the hatchery is reduced to a level that is not harmful to the hatching chicks.

Hatchery 10 also preferably includes means (not shown) for regulating the temperature of the internal atmosphere of hatchery 10. Means for regulating the temperature of the internal atmosphere may be, for example, a thermostat linked to heating and cooling means. The temperature may be any suitable temperature, preferably ambient temperature.

Hatchery 10 further preferably includes means (not shown) for applying a poultry gut serum to the egg following contact with and removal of the ozone.

In operation, at a predetermined time (such as two hours) before initial pip out, i.e., pip out of the first egg in the hatchery, the concentration of ozone in the internal atmosphere of hatchery 10 is increased, for example, by activating the means 14 for supplying a source of ozone and directing the flow of ozone through means 18 for introducing a source of ozone into hatchery 10. The concentration of ozone in the internal atmosphere of hatchery 10 is monitored by means 24 for determining the concentration of ozone and maintained by means (not shown) for regulating the concentration of ozone.

Means for regulating the concentration of ozone, preferably a computer, is adapted to communicate with means 14 for supplying a source of ozone and/or means 18 for introducing ozone. In a particularly preferred embodiment of the present invention, the computer regulates the concentration of ozone in the internal atmosphere of hatchery 10 by increasing or decreasing as appropriate the production of ozone by the means 14 and/or the flow of ozone through means 18 for introducing ozone. The concentration of ozone in the internal atmosphere of hatchery 10 is maintained at an effective level, such as from 2 to 4 ppm, for a time sufficient to control microorganisms on the egg or eggs.

The computer is also preferably adapted to communicate with means 42 for detecting pip out. When the first egg begins to hatch, i.e., initial pip out, means 42 for detecting pip out signals the computer, which in turn reduces the production of ozone by means 14 for supplying a source of ozone and/or the flow of ozone through means 18 for introducing ozone. The computer further activates means 30 for reducing the concentration of ozone, such as a ventilation scrubber system, and/or means 36 such as inlets, for introducing oxygen-rich gas and/or non-ozonated air from the external atmosphere.

Preferably, the computer also activates means (not shown) for applying a poultry gut serum to the egg following contact with and subsequent removal of the ozone.

A second embodiment of the present invention is directed to a method of controlling microorganisms on the surface of an egg. According to this embodiment of the present invention, the surface of the egg is contacted with an effective amount of a source of ozone for a time sufficient to control microorganisms on its surface. Preferably, the egg is a fertile egg and the source of ozone is ozonated air or gaseous ozone.

Another aspect of this embodiment of the present invention is directed to a system for controlling microorganisms on the surface of an egg. The inventive system comprises means for regulating the atmosphere surrounding the surface of an egg and means for introducing a source of ozone into this atmosphere.

Preferably, the means for regulating the atmosphere surrounding the surface of an egg is an enclosure dimensioned to contain one or more eggs. More preferably, the enclosure can be sealed to the external atmosphere.

Preferably, the source of ozone is ozonated air or gaseous ozone and the means for introducing a source of ozone is an ozone generator. More preferably, the source of ozone is sufficient to provide a level of from 2 to 4 ppm of ozone in the atmosphere surrounding the surface of the egg.

A third embodiment of the present invention is directed to a method of reducing the level of pathogen infection in a poultry flock. According to this embodiment of the present invention, the eggs that are to be hatched are contacted with a source of ozone for a time sufficient to control microorganisms on the surface of the eggs. More preferably, following contact with the source of ozone but before pip-out, a poultry gut serum is then applied to the surface of the eggs.

The source of ozone employed in this embodiment of the present invention is any suitable source of ozone, i.e., any source of ozone that will not harm or damage fertile eggs. Preferably, the source of ozone is ozonated air or gaseous ozone.

What is claimed is:

1. A method for reducing the level of pathogen infection in poultry comprising the steps of providing a source of ozone and contacting eggs to be hatched with an effective amount of said source of ozone for a time sufficient to control microorganisms on the surfaces of the eggs, and contacting the eggs with a poultry gut serum following said contact with a source of ozone, and further comprising the step of allowing hatching chicks to pip out and consume said poultry gut serum.

2. The method according to claim 1 wherein the poultry gut serum is a natural poultry gut serum.

3. The method according to claim 1 wherein the source of ozone is selected from ozonated air and gaseous ozone.

4. The method according to claim 1 wherein the poultry gut serum implants in the gut of the hatching chicks.

5. The method according to claim 1 wherein the amount of the source of ozone is sufficient to provide an ozone concentration of from 2 ppm to 4 ppm.

6. The method according to claim 1 operated at ambient pressure.

7. The method according to claim 6 wherein the ambient pressure is atmospheric pressure.

8. A system for controlling microorganisms comprising means for regulating an atmosphere surrounding a surface of an egg, means for introducing a source of ozone into this atmosphere, and further comprising means for detecting pip out of the egg, wherein said atmosphere is at atmospheric pressure.

9. The system according to claim 8 wherein the means for introducing a source of ozone is an ozone generator.

10. The system according to claim 8 further comprising means for reducing the concentration of ozone and means for introducing oxygen-rich air into the atmosphere.

11. The system according to claim 8 wherein the amount of the source of ozone is sufficient to provide an ozone concentration of from 2 ppm to 4 ppm.

* * * * *